US00PP26112P2

(12) United States Plant Patent
Delabroye

(10) Patent No.: US PP26,112 P2
(45) Date of Patent: Nov. 17, 2015

(54) ***HEUCHERA* PLANT NAMED 'PRETTY PERRINE'**

(50) Latin Name: ***Heuchera* hybrid**
Varietal Denomination: Pretty Perrine

(71) Applicant: Thierry Delabroye, Hantay (FR)

(72) Inventor: Thierry Delabroye, Hantay (FR)

(73) Assignee: SANDRINE DELABROYE, Hantay (FR)

( * ) Notice: Subject to any disclaimer, the term of this patent is extended or adjusted under 35 U.S.C. 154(b) by 95 days.

(21) Appl. No.: 13/694,476

(22) Filed: Dec. 5, 2012

(51) Int. Cl.
*A01H 5/12* (2006.01)

(52) U.S. Cl.
USPC ..... Plt./440

(58) Field of Classification Search
USPC ..... Plt./440
CPC ..... A01H 5/02; A01H 5/12; A01H 5/00; A01H 5/025
See application file for complete search history.

(56) References Cited

PUBLICATIONS

Gabot Plantarium 2011: Viele Neuheiten, retrieve on Aug. 5, 2014, retrieved from the Internet at <http://www.gabot.de/index.php/News-Details/52/0/?&tx_ttnews%5Btt_news%5D=218168tx_ttnews%5BbackPid%5D=1&cHash=6cffc84d7d> 9 pp.*
Google English translation of Gabot Plantarium 2011: Viele Neuheiten, 12 pp.*
Loader. Heucheraholics: New Heucheras, Heucherellas and Tiarellas coming to Heucheraholics soon. Heucheraholics the blog. Jun. 22, 2011, 3 pp.*
CPVO Application for grant of Community Plant Variety Rights to the Community Plant Variety Office for *Heuchera* 'Pretty Perrine' 2012, pp. 1-7.*

* cited by examiner

*Primary Examiner* — June Hwu
(74) *Attorney, Agent, or Firm* — Penny J Aguirre

(57) ABSTRACT

A new cultivar of hybrid *Heuchera* named 'Pretty Perrine', characterized by its foliage with leaves that are yellow-green with bright green veins and margins and light red mottling around the veins, its compact, upright, mounded plant habit, its white flowers with red tips on the petals held on thin strong green flowering stems, its tolerance to heat and humidity, and its vigorous growth habit.

2 Drawing Sheets

Botanical classification: *Heuchera* hybrid.
Cultivar designation: 'Pretty Perrine'.

CROSS REFERENCE TO A RELATED APPLICATION

This application is co-pending with a U.S. Plant Patent Application filed for a plant derived from the same breeding program that is entitled *Heuchera* Plant Named 'Circus' (U.S. Plant patent application Ser. No. 13/694,450).

BACKGROUND OF THE INVENTION

The present invention relates to a new and distinct cultivar of *Heuchera* of hybrid origin, botanically known as a *Heuchera* and is hereinafter referred to by its cultivar name 'Pretty Perrine'.

The new cultivar was discovered as a whole plant mutation by the Inventor in Hantay, France. The Inventor sowed seeds that were pooled from crosses made between unnamed proprietary plants his breeding program of *Heuchera*×*villosa* as the female parent and pollinated with 'Pinot Gris' (U.S. plant Pat. No. 19,592 as the male parent in 2008. The Inventor selected 'Pretty Perrine' in 2010 as a single unique plant amongst the seedlings that resulted from the above crosses. The exact female parent is unknown.

Asexual reproduction of the new cultivar was first accomplished by the Inventor by division in Hantay, France in 2011. Asexual reproduction of the new cultivar by division and tissue culture has shown that the unique features are stable and reproduced true to type in successive generations.

SUMMARY OF THE INVENTION

The following traits have been repeatedly observed and represent the characteristics of the new cultivar. These attributes in combination distinguish 'Pretty Perrine' as a new and unique cultivar of *Heuchera*.

1. 'Pretty Perrine' exhibits unique foliage with leaves that are yellow-green with bright green veins and margins and light red mottling around the veins.
2. 'Pretty Perrine' exhibits a compact, upright, mounded plant habit.
3. 'Pretty Perrine' exhibits white flowers with red tips on the petals held on thin strong green flowering stems.
4. 'Pretty Perrine' is tolerant to heat and humidity imparted by having *Heuchera*×*villosa* in its parentage.
5. 'Pretty Perrine' exhibits a vigorous growth habit.

'Pretty Perrine' is a unique *Heuchera* with foliage coloration that is unknown to exist in other cultivars of *Heuchera* known to the Inventor. 'Pretty Perrine' can be compared most closely to 'Tiramisu' (U.S. Plant Pat. No. 20,429), 'Circus', 'Pinot Gris' (male parent) and 'Electra' (U.S. Plant Pat. No. 21,856) for its similarity in having foliage that is marked with red and in having *Heuchera*×*villosa* in its parentage. 'Tiramisu' differs from 'Pretty Perrine' in having yellow-green foliage that is heavily mottled with red between the veins in cool temperature and green with silver mottling during the summer months and in having light pink flowers. 'Circus' differs from 'Pretty Perrine' in having leaves that are peach colored with reddish veining in spring and fall and lime green with a slight silver overlay and red veining in summer. 'Pinot Gris' differs from 'Pretty Perrine' in having foliage that emerges orange-yellow with a silver overlay and changes to a rosy grayed red with a silver overlay in summer. 'Electra' differs from 'Pretty Perrine' in having spring foliage that is bright yellow-gold with red veins and in having white flowers that lack red petal tips.

BRIEF DESCRIPTION OF THE DRAWING

The accompanying colored photographs illustrate the overall appearance and distinct characteristics of the new *Heuchera*. The photographs were taken of a plant two years in age as grown outdoors in a 10-liter container in The Netherlands.

The photograph in FIG. 1 provides a view of the plant habit of 'Pretty Perrine' in bloom.

Figure 1:
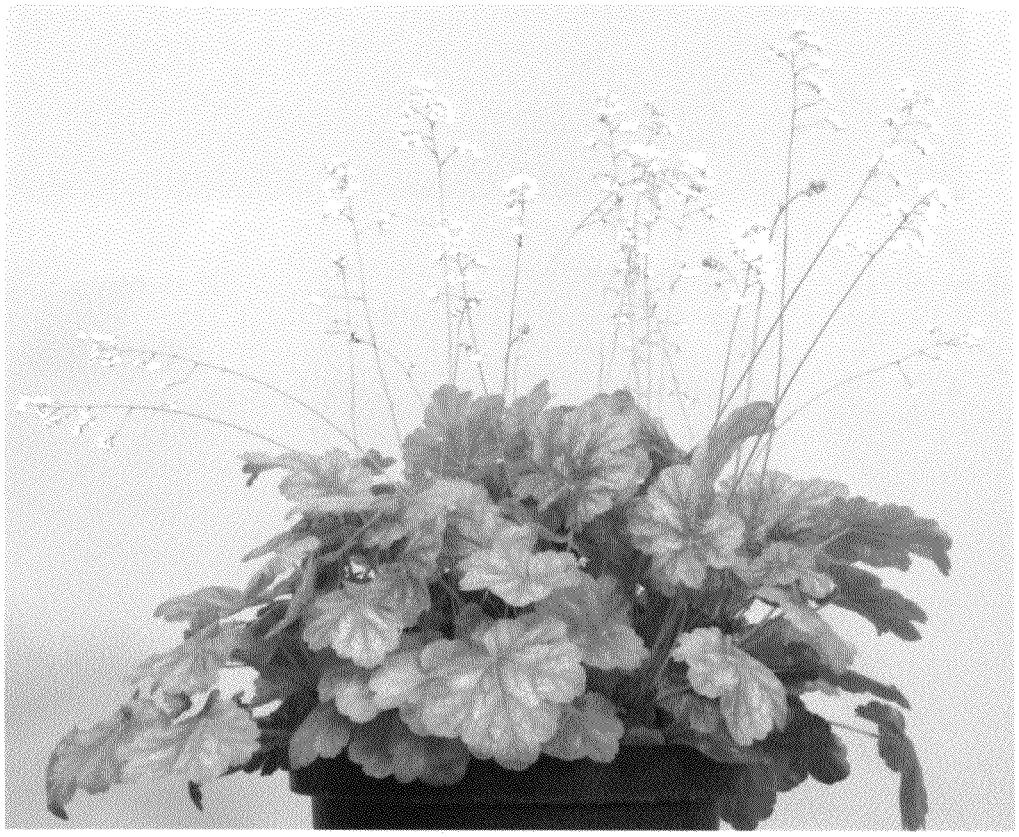
Figure 2:
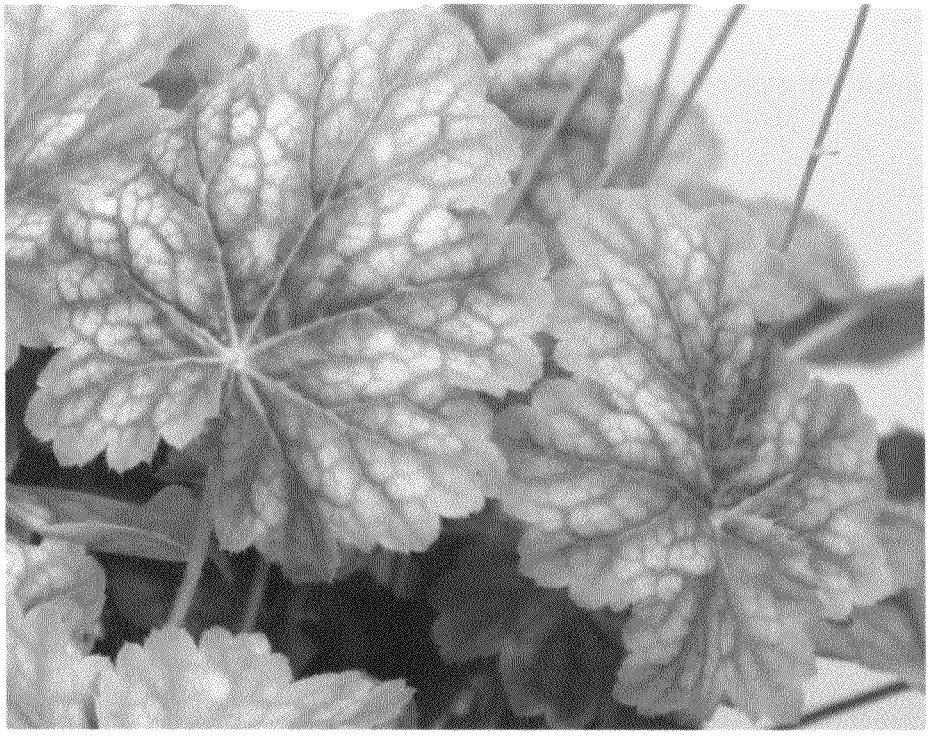

The photograph in FIG. 2 provides a close-up view of the foliage of 'Pretty Perrine'.

Figure 3:
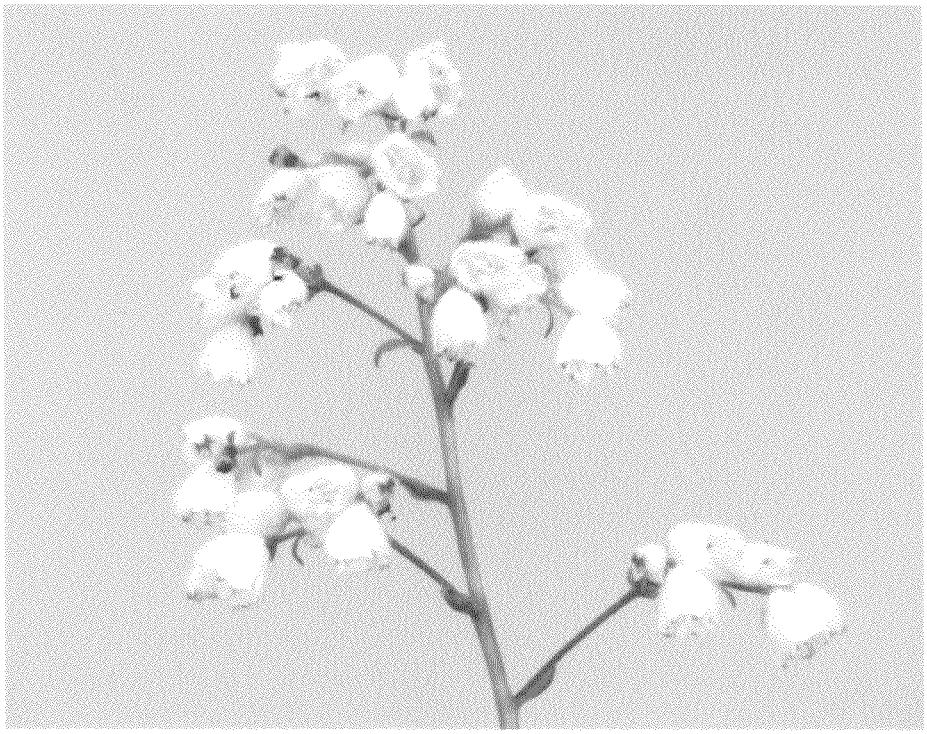

The photograph in FIG. 3 provides a close-up view of the flowers of 'Pretty Perrine'.

The colors in the photographs are as close as possible with the digital photography techniques available, the color values cited in the detailed botanical description accurately describe the colors of the new *Heuchera*.

DETAILED BOTANICAL DESCRIPTION OF THE PLANT

The following is a detailed description of 2-year old plants of the new cultivar as grown outdoors in 10-liter containers in The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Early to mid summer in The Netherlands.

*Plant type*.—Perennial, herbaceous to semi-evergreen.

*Plant habit*.—Compact, clump-forming, mounded foliage.

*Height and spread*.—Average of 27 cm in height from soil to top of leaves and 48 cm from soil to top of inflorescences, and about 52.5 cm in width.

*Cold hardiness*.—At least to U.S.D.A. Zone 3.

*Diseases and pests*.—Not more susceptible to pests and diseases than other *Heuchera* varieties.

*Environmental stresses*.—Tolerant to heat and humidity.

*Root description*.—Fibrous roots on woody rootstalks.

*Branching habit*.—Basal rosette, flowering stems arise from the rosettes.

*Propagation*.—In vitro propagation is the preferred method, division are also possible.

*Growth rate*.—Vigorous.

Stem description (flowering stem or primary peduncle):

*Shape*.—Round.

*Stem color*.—144A.

*Stem size*.—An average of 1.5 mm in diameter and 31.5 cm in length.

*Stem strength*.—Strong.

*Stem aspect*.—Flowering stems grow in an average angle of 65° to base (0°=horizontal).

*Stem surface*.—Moderately glossy, rounded, moderately to densely covered with short hairs, average of 0.5 mm in length and NN155D in color.

*Stem number*.—Average of 30 flowering stems.

*Branching*.—Main stem with an average of 3 rosettes.

Foliage description:

*Leaf shape*.—Broad ovate to orbicular.

*Leaf division*.—Simple.

*Leaf base*.—Hastate, slightly overlapping.

*Leaf apex*.—Obtuse to mucronulate.

*Leaf venation*.—Laciniate, 145A on upper surface, 145C to 145D on lower surface.

*Leaf margins*.—Lobed with average of 9 lobes per leaf, lobe margins crenate, main veins on underside sparsely covered with short hairs 0.8 mm in length and NN155D in color.

*Leaf attachment*.—Petiolate.

*Leaf arrangement*.—Alternate, basal rosettes.

*Leaf orientation*.—Typically nearly horizontal to petiole.

*Leaf surface*.—Both surfaces dull, some sparse pubescence on upper side and on main veins on underside, 0.8 mm in length and NN155D in color.

*Leaf color*.—Young upper surface; between 172A and 177B, margins between 144B and N144B, young lower surface; 174A, margins 145A, mature upper surface; between 150B and 151D, area near the veins tinged 199A, with margins N144A. mature lower surface; 145B to 145C.

*Leaf size*.—Average of 9.8 cm in length and 9.3 cm in width.

*Leaf quantity*.—16 per basal rosette.

*Petioles*.—Round in shape, average of 13.3 cm in length and 2 mm in width, color; 145A.

*Stipules*.—Leafy stipules at the base of each leaf, lanceolate in shape, narrow acute apex, truncate base, glabrous surface, an average of 1.5 cm in length and 4 mm in width and 70B in color.

Flower description:

*Inflorescence type*.—Numerous small bell-shaped flowers arranged on pyramidal panicles on flower scapes emerging from the base of the rosette.

*Inflorescence size*.—An average of 9.0 cm in height (excluding peduncle) and about 5.5 cm in width.

*Inflorescence number*.—An average of 30 per 10-liter container.

*Flower fragrance*.—None.

*Flower quantity*.—Average of 40 flowers per flowering stem.

*Flower lastingness*.—Average of one week.

*Flower buds*.—Broad ovate in shape, an average of 4 mm in length and 2 mm in diameter, color; a blend of 155A and157D, apex 59A.

*Flower aspect*.—Drooping to outward.

*Flower type*.—Campanulate.

*Flower size*.—About 6 mm in diameter and 6 mm in depth (height).

*Petals*.—About 5, rotate arrangement and implanted in the hypanthium, oblanceolate in shape, margin is entire, apex is acute, upper and lower surface is dull and smooth, color of upper and lower surface when opening; 155D with tips 59A, upper and lower surface when fully open; NN155C to NN155D with small tip of 59A, about 3 mm in length and 1 mm in width.

*Calyx*.—Campanulate, sepals fused to hypanthium, 6 mm in depth and diameter.

*Sepals*.—5, fused, campanulate hypanthium, elliptic in shape, about 6 mm in length and 2 mm in width, margin is entire, apex is broadly acute, fused base, dull on upper and lower surface with lower surface is moderately covered with very short glandular hairs about 0.1 mm in length and NN155D in color, color: immature upper and lower surface; 155D, apex 58A, mature upper and lower surface; NN155C to NN155D, apex 58C.

*Peduncles*.—Rachis; average of 7.9 cm in length and 1 mm in width, moderate strength, held at a 0° angle (straight on top of flowering stem), color 144B, secondary peduncles; average of 1.5 cm in length, 0.75 mm in diameter, moderate in strength, held at a 60° (0°=straight upright) to rachis, color 144B, surfaces moderately glossy, rounded, moderately to densely covered with short hairs, average of 0.5 mm in length and NN155D in color.

*Pedicels*.—Average of 2 mm in length and 0.3 mm in width, moderate in strength, color of both surfaces 144B, pedicel of primary flower of each spikelet straight on top of secondary pedicel, pedicels of secondary and tertiary flowers of each spikelet in an average angle of 45° (0°=straight on top of secondary peduncle), surface moderately glossy, rounded, moderately to densely covered with short hairs, average of 0.5 mm in length and NN155D in color.

*Bracts*.—1 at the base of each secondary peduncle, lanceolate in shape, narrow acute apex, truncate base, an average of 7 mm in length and 2 mm in width, glabrous surface, and 144A in color.

Reproductive organs:

*Gynoecium*.—2 pistils, about 3 mm in length, stigmas pointed in shape and NN 155D in color, styles are about 2.5 mm in length and about NN155D in color, ovaries are 155A in color.

*Androcoecium*.—About 5 stamens, anthers are ovate in shape, about 0.25 mm in length and 164C in color, filament is 2 mm in length and NN155C to NN155D in color, pollen is low in quantity and 160D in color.

*Seed/fruit*.—No fruit or seeds detected to date.

It is claimed:

1. A new and distinct cultivar of hybrid *Heuchera* plant named 'Pretty Perrine' as herein illustrated and described.

* * * * *